(12) United States Patent
Carriere et al.

(10) Patent No.: US 10,502,688 B2
(45) Date of Patent: *Dec. 10, 2019

(54) IDENTIFICATION AND ANALYSIS OF MATERIALS AND MOLECULAR STRUCTURES

(71) Applicant: Ondax, Inc., Monrovia, CA (US)

(72) Inventors: James Carriere, La Crescenta, CA (US); Lawrence Ho, Arcadia, CA (US); Frank Havermeyer, La Verne, CA (US); Eric Maye, Torrance, CA (US); Randy Heyler, Newport Beach, CA (US)

(73) Assignee: Ondax, Inc., Monrovia, CA (US)

( * ) Notice: Subject to any disclaimer, the term of this patent is extended or adjusted under 35 U.S.C. 154(b) by 260 days.

This patent is subject to a terminal disclaimer.

(21) Appl. No.: 15/464,114

(22) Filed: Mar. 20, 2017

(65) Prior Publication Data

US 2017/0191939 A1 Jul. 6, 2017

Related U.S. Application Data

(63) Continuation of application No. 14/044,773, filed on Oct. 2, 2013, now Pat. No. 9,599,565.

(51) Int. Cl.
| | |
|---|---|
| *G01J 3/44* | (2006.01) |
| *G01N 21/65* | (2006.01) |
| *G01N 21/3581* | (2014.01) |

(52) U.S. Cl.
CPC ......... *G01N 21/65* (2013.01); *G01N 21/3581* (2013.01); *G01N 2201/068* (2013.01); *G01N 2201/06113* (2013.01)

(58) Field of Classification Search
CPC ........... C08F 2/00; C08F 10/00; G01N 21/65; G01N 2021/656; G01N 21/3581;
(Continued)

(56) References Cited

U.S. PATENT DOCUMENTS

| | | |
|---|---|---|
| 3,588,254 A | 6/1971 | Rhoades |
| 3,588,738 A | 6/1971 | Goodwin |
| (Continued) | | |

FOREIGN PATENT DOCUMENTS

| | | |
|---|---|---|
| DE | 4214014 A1 | 11/1992 |
| DE | 102012203717 A1 | 3/2013 |

OTHER PUBLICATIONS

Askins, "Fiber Bragg refractors prepared by a single excimer pulse," Opt. Lett., vol. 17(11), pp. 833-835 (1992).
(Continued)

*Primary Examiner* — Sunghee Y Gray
(74) *Attorney, Agent, or Firm* — Carr & Ferrell LLP

(57) ABSTRACT

Provided are methods and systems for identification and analysis of materials and molecular structures. An apparatus for identification and analysis of materials and molecular structures may include a laser. The laser may, in turn, include an amplified spontaneous emission-suppressed single-frequency laser excitation source. The apparatus may further comprise a plurality of filters. The plurality of filters may include reflective volume holographic grating blocking filters. The apparatus may also comprise an optical unit and an optical spectrometer. The optical unit may be configured to deliver excitation energy to a sample substance and capture Raman signal scattering from the sample substance. The optical spectrometer may be disposed in a path of the Raman signal and configured to measure a spectrum of the Raman signal and generate a detection signal. Finally, the apparatus may comprise a processing unit configured to analyze the spectrum.

15 Claims, 14 Drawing Sheets

(58) Field of Classification Search
CPC .......... G01J 3/44; G01J 3/1838; G01J 3/0227; G01J 3/443
USPC ........................................................ 356/301
See application file for complete search history.

(56) References Cited

U.S. PATENT DOCUMENTS

| | | |
|---|---|---|
| 3,659,947 A | 5/1972 | Neumann |
| 3,902,135 A | 8/1975 | Terada et al. |
| 4,017,144 A | 4/1977 | Staebler |
| 4,057,408 A | 11/1977 | Pierson et al. |
| 4,103,254 A | 7/1978 | Chikami |
| 4,181,515 A | 1/1980 | Dyott et al. |
| 4,456,328 A | 6/1984 | Arns et al. |
| 4,794,344 A | 12/1988 | Johnson |
| 4,807,950 A | 2/1989 | Glenn et al. |
| 4,824,193 A | 4/1989 | Maeda et al. |
| 4,834,474 A | 5/1989 | George et al. |
| 4,942,583 A | 7/1990 | Nazarathy et al. |
| 5,042,898 A | 8/1991 | Morey et al. |
| 5,107,365 A | 4/1992 | Ota |
| 5,115,344 A | 5/1992 | Jaskie |
| 5,221,957 A | 6/1993 | Jannson et al. |
| 5,315,417 A | 5/1994 | Moss et al. |
| 5,335,098 A | 8/1994 | Leyva et al. |
| 5,388,173 A | 2/1995 | Glenn |
| 5,432,623 A | 7/1995 | Egan et al. |
| 5,440,669 A | 8/1995 | Rakuljic et al. |
| 5,491,570 A | 2/1996 | Rakuljic et al. |
| 5,499,134 A | 3/1996 | Galvanauskas et al. |
| 5,517,525 A | 5/1996 | Endo et al. |
| 5,594,744 A | 1/1997 | Lefevre et al. |
| 5,625,453 A | 4/1997 | Matsumoto et al. |
| 5,636,304 A | 6/1997 | Mizrahi et al. |
| 5,640,256 A | 6/1997 | De Vre et al. |
| 5,657,121 A | 8/1997 | Nishina |
| 5,684,611 A | 11/1997 | Rakuljic et al. |
| 5,691,989 A | 11/1997 | Rakuljic et al. |
| 5,771,250 A | 6/1998 | Shigehara et al. |
| 5,796,096 A | 8/1998 | Rakuljic et al. |
| 5,844,700 A | 12/1998 | Jeganathan et al. |
| 5,917,648 A | 6/1999 | Harker |
| 5,943,128 A | 8/1999 | Slater |
| 5,960,133 A | 9/1999 | Tomlinson |
| 5,966,391 A | 10/1999 | Zediker et al. |
| 6,044,285 A | 3/2000 | Chaiken et al. |
| 6,049,554 A | 4/2000 | Lang et al. |
| 6,100,975 A | 8/2000 | Smith et al. |
| 6,101,301 A | 8/2000 | Engelberth et al. |
| 6,139,146 A | 10/2000 | Zhang |
| 6,147,341 A | 11/2000 | Lemaire et al. |
| 6,169,829 B1 | 1/2001 | Laming et al. |
| 6,192,062 B1 | 2/2001 | Sanchez-Rubio et al. |
| 6,211,976 B1 | 4/2001 | Popovich et al. |
| 6,221,535 B1 | 4/2001 | Cox et al. |
| 6,226,084 B1 | 5/2001 | Tormod |
| 6,249,624 B1 | 6/2001 | Putnam |
| 6,281,974 B1 | 8/2001 | Scheiner |
| 6,304,687 B1 | 10/2001 | Inoue et al. |
| 6,327,283 B1 | 12/2001 | Hung |
| 6,327,292 B1 | 12/2001 | Sanchez-Rubio et al. |
| 6,339,504 B1 | 1/2002 | Oliva |
| 6,339,609 B2 | 1/2002 | Lefevre |
| 6,356,684 B1 | 3/2002 | Patterson et al. |
| 6,363,187 B1 | 3/2002 | Fells et al. |
| 6,370,310 B1 | 4/2002 | Jin et al. |
| 6,396,982 B1 | 5/2002 | Lin |
| 6,414,973 B1 | 7/2002 | Hwu et al. |
| 6,449,097 B1 | 9/2002 | Zhu et al. |
| 6,498,872 B2 | 12/2002 | Bouevitch et al. |
| 6,498,891 B1 | 12/2002 | Montesanto et al. |
| 6,507,693 B2 | 1/2003 | Maron et al. |
| 6,512,618 B1 | 1/2003 | Heflinger |
| 6,568,220 B1 | 5/2003 | Paek et al. |
| 6,586,141 B1 | 7/2003 | Efimov et al. |
| 6,587,180 B2 | 7/2003 | Wang et al. |
| 6,606,152 B2 | 8/2003 | Littau et al. |
| 6,621,957 B1 | 9/2003 | Sullivan et al. |
| 6,628,862 B1 | 9/2003 | Yao |
| 6,670,079 B1 | 12/2003 | Kitamura et al. |
| 6,673,497 B2 | 1/2004 | Efimov et al. |
| 6,714,309 B2 | 3/2004 | May |
| 6,750,996 B2 | 6/2004 | Jagt et al. |
| 6,768,577 B2 | 7/2004 | Eggleton et al. |
| 6,788,849 B1 | 9/2004 | Pawluczyk |
| 6,822,218 B2 | 11/2004 | Helmig et al. |
| 6,828,262 B2 | 12/2004 | Borrelli et al. |
| 6,829,067 B2 | 12/2004 | Psaltis et al. |
| 6,844,946 B2 | 1/2005 | Buse et al. |
| 6,847,763 B2 | 1/2005 | Eggleton et al. |
| 6,879,441 B1 | 4/2005 | Mossberg |
| 6,904,200 B2 | 6/2005 | Wang et al. |
| 6,934,060 B2 | 8/2005 | Psaltis |
| 6,987,907 B2 | 1/2006 | Psaltis et al. |
| 6,992,805 B2 | 1/2006 | Ingwall et al. |
| 7,002,697 B2 | 2/2006 | Domash et al. |
| 7,031,573 B2 | 4/2006 | Volodin et al. |
| 7,081,977 B2 | 7/2006 | Kim |
| 7,081,978 B2 | 7/2006 | Chen |
| 7,125,632 B2 | 10/2006 | Volodin et al. |
| 7,136,206 B2 | 11/2006 | Psaltis et al. |
| 7,173,950 B2 | 2/2007 | Hand et al. |
| 7,212,554 B2 | 5/2007 | Zucker et al. |
| 7,245,369 B2 | 7/2007 | Wang et al. |
| 7,245,407 B2 | 7/2007 | Komma |
| 7,248,617 B2 | 7/2007 | Volodin et al. |
| 7,248,618 B2 | 7/2007 | Volodin et al. |
| 7,273,683 B2 | 9/2007 | Volodin et al. |
| 7,298,771 B2 | 11/2007 | Volodin et al. |
| 7,355,768 B1 | 4/2008 | Billmers et al. |
| 7,359,046 B1 | 4/2008 | Steckman et al. |
| 7,359,420 B2 | 4/2008 | Shchegrov et al. |
| 7,372,565 B1 | 5/2008 | Holden et al. |
| 7,391,703 B2 | 6/2008 | Volodin et al. |
| 7,397,837 B2 | 7/2008 | Volodin et al. |
| 7,398,119 B2 | 7/2008 | Lambert et al. |
| 7,424,185 B2 | 9/2008 | Glebov et al. |
| 7,477,818 B2 | 1/2009 | Volodin et al. |
| 7,483,190 B2 | 1/2009 | Psaltis et al. |
| 7,528,385 B2 | 5/2009 | Volodin et al. |
| 7,542,639 B2 | 6/2009 | Moser et al. |
| 7,545,844 B2 | 6/2009 | Volodin et al. |
| 7,548,313 B2 | 6/2009 | Nguyen |
| 7,570,320 B1 | 8/2009 | Anderson et al. |
| 7,590,162 B2 | 9/2009 | Volodin et al. |
| 7,605,911 B2 | 10/2009 | Wieloch et al. |
| 7,633,985 B2 | 12/2009 | Volodin et al. |
| 7,636,376 B2 | 12/2009 | Moser et al. |
| 7,639,718 B1 | 12/2009 | Moser et al. |
| 7,667,882 B2 | 2/2010 | Adibi et al. |
| 7,697,589 B2 | 4/2010 | Volodin et al. |
| 7,719,675 B2 | 5/2010 | Grygier et al. |
| 7,746,480 B2 | 6/2010 | Ozcan et al. |
| 7,792,003 B2 | 9/2010 | Volodin et al. |
| 7,796,673 B2 | 9/2010 | Volodin et al. |
| 7,817,888 B2 | 10/2010 | Volodin et al. |
| 7,822,347 B1 | 10/2010 | Brennan, III et al. |
| 7,830,507 B2 | 11/2010 | Brady et al. |
| 7,986,407 B2 | 7/2011 | Moser et al. |
| 8,049,885 B1 | 11/2011 | Moser et al. |
| 8,139,212 B2 | 3/2012 | Moser et al. |
| 8,184,285 B2 | 5/2012 | Moser et al. |
| 8,369,017 B2 | 2/2013 | Moser et al. |
| 8,384,992 B2 | 2/2013 | Moser et al. |
| 9,097,896 B2 | 8/2015 | Moser et al. |
| 9,587,983 B1 | 3/2017 | Ho et al. |
| 9,599,565 B1 | 3/2017 | Carriere et al. |
| 2001/0050751 A1 | 12/2001 | Banyai et al. |
| 2001/0055094 A1 | 12/2001 | Zhang |
| 2002/0012377 A1 | 1/2002 | Suganuma et al. |
| 2002/0015376 A1 | 2/2002 | Liu et al. |
| 2002/0045104 A1 | 4/2002 | Efimov et al. |
| 2002/0093701 A1 | 7/2002 | Zhang et al. |
| 2002/0141063 A1 | 10/2002 | Petrov et al. |

(56) References Cited

U.S. PATENT DOCUMENTS

| | | |
|---|---|---|
| 2002/0154315 A1 | 10/2002 | Myrick |
| 2002/0176457 A1 | 11/2002 | DeCusatis et al. |
| 2002/0181035 A1 | 12/2002 | Donoghue |
| 2003/0007202 A1 | 1/2003 | Moser et al. |
| 2003/0011833 A1 | 1/2003 | Yankov et al. |
| 2003/0072336 A1 | 4/2003 | Senapati et al. |
| 2003/0128370 A1 | 7/2003 | De Lega |
| 2003/0156607 A1 | 8/2003 | Lipson et al. |
| 2003/0165639 A1 | 9/2003 | Park |
| 2003/0169787 A1 | 9/2003 | Vurgaftman et al. |
| 2003/0190121 A1 | 10/2003 | Luo et al. |
| 2003/0210863 A1 | 11/2003 | Myers et al. |
| 2003/0231305 A1 | 12/2003 | Zeng |
| 2004/0021920 A1 | 2/2004 | Psaltis |
| 2004/0127778 A1 | 7/2004 | Lambert et al. |
| 2004/0165639 A1 | 8/2004 | Lang et al. |
| 2004/0191637 A1 | 9/2004 | Steckman et al. |
| 2004/0253751 A1 | 12/2004 | Salnik et al. |
| 2004/0258356 A1 | 12/2004 | Brice et al. |
| 2005/0018743 A1 | 1/2005 | Volodin et al. |
| 2005/0129072 A1 | 6/2005 | Tayebati et al. |
| 2005/0196876 A1 | 9/2005 | Chan et al. |
| 2005/0206984 A1 | 9/2005 | Kawano |
| 2005/0226636 A1 | 10/2005 | Hiramatsu et al. |
| 2005/0248819 A1 | 11/2005 | Hymel et al. |
| 2005/0248820 A1 | 11/2005 | Moser et al. |
| 2005/0270607 A1 | 12/2005 | Moser et al. |
| 2005/0275837 A1 | 12/2005 | Zhang et al. |
| 2006/0014799 A1 | 1/2006 | Whittle et al. |
| 2006/0029120 A1 | 2/2006 | Mooradian et al. |
| 2006/0098258 A1 | 5/2006 | Chen |
| 2006/0114955 A1 | 6/2006 | Steckman |
| 2006/0156241 A1 | 7/2006 | Psaltis et al. |
| 2006/0251143 A1 | 11/2006 | Volodin et al. |
| 2006/0256830 A1 | 11/2006 | Volodin et al. |
| 2006/0280209 A1 | 12/2006 | Treusch et al. |
| 2007/0047608 A1 | 3/2007 | Volodin et al. |
| 2007/0064304 A1 | 3/2007 | Brennan et al. |
| 2007/0160325 A1 | 7/2007 | Son et al. |
| 2007/0279627 A1 | 12/2007 | Tack et al. |
| 2009/0186947 A1* | 7/2009 | Fischer ............... C07C 215/54 514/654 |
| 2010/0027001 A1 | 2/2010 | Moser et al. |
| 2010/0103489 A1 | 4/2010 | Moser et al. |
| 2010/0110429 A1 | 5/2010 | Simoni et al. |
| 2010/0149647 A1 | 6/2010 | Figueroa et al. |
| 2011/0216316 A1 | 9/2011 | Moser et al. |
| 2011/0216384 A1 | 9/2011 | Moser et al. |
| 2012/0002197 A1 | 1/2012 | Moser et al. |
| 2012/0044554 A1 | 2/2012 | Moser et al. |
| 2012/0085900 A1 | 4/2012 | Verbeck |
| 2012/0200851 A1 | 8/2012 | Wu |
| 2015/0030503 A1* | 1/2015 | Angel ..................... G01J 3/44 422/82.05 |
| 2016/0109373 A1* | 4/2016 | Pan ..................... G01N 21/87 356/30 |
| 2017/0082489 A1 | 3/2017 | Ho et al. |

OTHER PUBLICATIONS

Bochove, E.J. et al. "Theory of Spectral Beam Combining of Fiber Lasers," IEEE J. Quant. Elec., 38:5 (2002).

Bosomworth et al. "Thick holograms in photochromic material" Applied Optics [Online] 1968, 7(1), Abstract.

Burr, Geoffrey et al. "Angle and Space Multiplexed Holographic Storage Using the 90 degree Geometry," Optics Comm. 117 (1995).

Curtis, Kevin et al. "Cross Talk for Angle- and Wavelength-Multiplexed Image Plane Holograms," Optics Letters. vol. 19 (21) (1994).

Daneu, V. et al. "Spectral Beam Combining of a Broad-Stripe Diode Laser Array in an External Cavity," Opt. Lett. 25:6 (2000).

Dos Santos, Paulo et al. "Interference-term Real-time Measurement for Self-stablized Two-wave Mixing in Photorefractive Crystals," Optics Letters, Nov. 1988, vol. 13, No. 11, pp. 1014-1016.

Erdei et al. "Optimization method for the design of beam shaping systems" Optical Engineering [Online] 2002, 41, Abstract.

Ford, Joseph et al. "Wavelength Add-Drop Switching Using Tilting Micromirrors," Journal of Lightwave Technology, vol. 17, No. 5 (May 1999).

Frejlich, Jamie et al. "Analysis of an Active Stabliziation System for a Holographic Setup," Applied Optics, May 15, 1988, vol. 27, No. 10, pp. 1967-1976.

Goodman, Joseph W. "Introduction to Fourier Optics," 1968, pp. 198-224.

Havermeyer, Frank et al. "Volume Holographic Grating-Based Continuously Tunable Optical Filter," Opt. Eng. 43(9), Sep. 2004, pp. 2017-2021.

Heaney et al., "Sol-gel derived photosensitive germanosilicate glass monoliths," Opt. Lett., vol. 25(24), pp. 1765-1767 (Dec. 2000).

Hill, "Photosensitivity in optical fiber waveguides: Application to reflection filter fabrication," Appl. Opt. Lett. vol. 32(10), pp. 647-649 (1978).

Hill, "Simple Transient Holograms in Ruby," Appl. Opt., vol. 10(7), pp. 1695-1697 (1971).

In re Rose, 220 F.2d 459, 105 USPQ 237-241 (CCPA 1955).

Kogelnik, Herwig. "Coupled Wave Theory for Thick Hologram Gratings," The Bell System Tech. Journal, Nov. 1969, vol. 48, No. 9, pp. 2909-2947.

Levene, Michael et al. "Method for Controlling the Shift Invairance of Optical Correlators," Applied Optics, Jan. 10, 1999, vol. 38, No. 2, pp. 394-398.

Li, Lijun et al. "Experimental Studies on Narrow-Linewidth YB3+-Doped Double-Clad Fiber-Laser Cavities Based on Double-Clad Fiber Bragg Gratings," Microwave and Optical Technology Letters, 44(1):53-56 (2005).

Littman, Michael G. "Singlemode Operation Grazing-Incidence Pulsed Dye Laser," Optics Letters, Oct. 1978, vol. 3, pp. 138-140.

Mill, P. "Single Mode Operation of a 1.55 Micrometer Semiconductor Lasers Using a Volume Holographic Grating," Jul. 1985, Electronics Letters, pp. 648-649.

Mitchard, Gordon et al. "Double-Clad Fibers Enable Lasers to Handle High Power," Laser Focus World. Jan. 1999, 2 pages.

Miyazaki, T. et al. "Nd-Doped Double-Clad Fiber Amplifier at 1.06um," Journal of Lightwave Technology, 16(4): 562-566 (Apr. 1998).

Moser, Christophe. "Folded Shift Multiplexing," Optics Letters, vol. 28 (11) (Jun. 2003).

Sadot, D. et al. "Tunable Optical Filters for Dense WDM Networks," IEEE Communications Magazine, 50-55 (1998).

Saleh, B. and M. Teich, "Fundamentals of Photonics," Wiley-Interscience, p. 151, 631-632 (1991).

Shu et al. "More on analyzing the reflection of a laser beam by a deformed highly reflective volume Bragg grating using iteration of the beam propagation method" Applied Optics [Online] 2009, 48 (1) , pp. 22-27.

Smith, Warren. "Modern Optical Engineering," 1990, pp. 43-47.

Steckman, Gregory J. et al. "Holographic Data Storage in Phenanthrenequinone Doped PMMA," SPIE Photonics Nest, San Jose, CA (Jan. 27, 1999), pp. 234-242.

Steckman, Gregory J. et al. "Holographic Multiplexing in Photorefractive Polymers," Optics Communications, Nov. 1, 2000, 185, pp. 13-17.

Steckman, Gregory J. et al. "Storage Density of Shift-Multiplexed Holographic Memory," Applied Optics, Jul. 10, 2001, vol. 40, No. 20, pp. 3387-3394.

Venus, George et al. "Semiconductor 1.7 W Volume Bragg Laser with Divergence Close to a Diffraction Limit," 26th Annual Conference on Lasers and Electro-Optics. CLEO/IQES and PhAST Technical Digest, Paper Code CFG4, Long Beach, CA, May 2006, 3 pages.

Volodin, B.L. et al. "Wavelength Stabilization and Spectrum Narrowing of High-Power Multimode Laser Diodes and Arrays by Use of Volume Bragg Gratings," Optics Letters, vol. 29, No. 16 (Aug. 15, 2004), pp. 1891-1893.

(56) References Cited

OTHER PUBLICATIONS

Yiou, Silvie et al. "Improvement of the Spatial Beam Quality of Laser Sources with an Intracavity Bragg Grating," Opt. Lett, 28 (4), 242-244 (2003).
Zorabedian, Paul. "Tunable Lasers Handbook—tunable external-davity semi-conductor lasers," Chapter 8, Academic Press (1995), pp. 398-404.
Laux et al. "Holographic bulk grating photopolymer for pulse stretching in a CPA laser," CLEO Europe (2007), 1 page.

\* cited by examiner

IDENTIFICATION AND ANALYSIS OF MATERIALS AND MOLECULAR STRUCTURES

CROSS-REFERENCE TO RELATED APPLICATIONS

The present application is a continuation of, and claims the priority benefit of, U.S. Nonprovisional patent application Ser. No. 14/044,773, filed Oct. 2, 2013, titled "Identification and Analysis of Materials and Molecular Structures", now U.S. Pat. No. 9,599,565, issued on Mar. 21, 2017. The disclosure of the above application is hereby incorporated by reference in its entirety, including all references cited therein.

TECHNICAL FIELD

This disclosure relates generally to chemical analysis using Raman spectroscopy and, more specifically, to the use of low-frequency Raman spectra and simultaneous acquisition of low-frequency Stokes and anti-Stokes spectra.

BACKGROUND

The approaches described in this section could be pursued but are not necessarily approaches that have previously been conceived or pursued. Therefore, unless otherwise indicated, it should not be assumed that any of the approaches described in this section qualify as prior art merely by virtue of their inclusion in this section.

Chemical polymorph detection, identification, and analysis may be an important process in many industries that rely on formulation, inspection, analysis, or process/quality control of chemicals or materials, for example, in pharmaceuticals, petrochemicals, electronics, solar technology and photovoltaics, food processing, industrial chemicals, and so forth. Additionally, reliable and reproducible detection, analysis, formulation, manufacturing or testing of materials, such as biological, chemical, semiconductors, geological materials, may require both chemical and structural analysis of the substance. Currently, various spectroscopic techniques may be used to attempt to identify chemical constituents, including mass spectroscopy (MS), Fourier transform infrared (FT-IR), near-infrared (FT-NIR) spectroscopy, Terahertz (THz, or far-IR) spectroscopy, and Raman spectroscopy.

Various techniques may be used to identify characteristics related to material structure (e.g., crystal structure and polymeric chain orientation), including x-ray diffraction (XRD), THz spectroscopy, scanning electron microscopy (SEM), and atomic force or scanning probe microscopy (AFM/SPM).

Typically, Raman and infrared (IR) spectroscopic techniques measure spectral signals, also referred to as "Raman shifts", across what is referred to a "fingerprint region" ranging from ~200 $cm^{-1}$ to 5,000 $cm^{-1}$ (or 6 THz-150 THz), where the shifts (measured relative to an excitation wavelength) have been correlated to specific vibration energies associated with various chemical bonds, leading to a decipherable signature related to the chemical composition of the substance. After measurements are taken, a library of reference spectra may be used for comparison, and, furthermore, sophisticated algorithms may be used to analyze both the composition and concentration of compounds.

Low frequency Raman shifts, which also correspond to what is referred to as "THz-regime" frequencies (defined as ranging from ~5 $cm^{-1}$ to 200 $cm^{-1}$, or 150 GHz to 6 THz), have been shown to provide additional information (beyond chemical composition) relating to specific lattice vibrations or "phonon modes" that are indicative of molecular structure, and therefore are more directly informative about crystal lattices or polymeric chain orientations, as well as intermolecular interactions of molecules. These low frequency/THz spectra, also referred to as THz-Raman spectra, may be used to rapidly and clearly distinguish polymorphs, allotropes, conformers, or other structurally distinctive attributes of materials in a variety of substances, including pharmaceuticals, plastics and polymers, industrial chemicals, explosive and hazardous materials, nano-materials, biological tissues, and so forth.

However, these frequencies, which reside extremely close to the Rayleigh (or excitation) wavelength, have been both difficult and expensive to access with traditional Raman spectrometer systems. Rayleigh attenuation is critical to all Raman systems, since the process of Raman scattering is extremely inefficient, in particular, only about $1\times10^{-9}$ of the incident photons will produce a Raman signal. Accordingly, in order to resolve these extremely weak signals, the excitation wavelength typically needs to be attenuated with a filter achieving an optical density (OD) of OD 8.

Most commercial Raman systems utilize thin film edge filters to completely remove the Rayleigh excitation. The thin film edge filters may cut off all signals below about 150-200 $cm^{-1}$ from the Rayleigh line, blocking both low frequencies and the entire anti-Stokes region. Some systems utilize notch filters (either thin-film or holographic), which can enable capture of anti-Stokes signals, but limitations on their transition bandwidth also result in blocking low-frequency signals. These systems are well suited to examining higher-energy molecular transitions (from ~200 $cm^{-1}$ to 2,500 $cm^{-1}$) for chemical composition, with sufficiently broad range and spectral resolution (~5 to 10 $cm^{-1}$ or 150 to 300 GHz) for most chemical identification and analysis applications, but cannot capture low-frequency signals.

Multi-stage, or cascaded, spectrometer systems have been the traditional means for achieving extremely high Rayleigh reduction while preserving the low-frequency signals that are close to the laser line, but these traditional systems significantly increase the size and complexity of the system, while greatly reducing the overall Raman signal as well. Therefore, low-frequency measurements may take extremely long periods and may be susceptible to poor signal-to-noise ratios (SNR). These systems may be also quite large, expensive and require a great deal of expertise to operate, thus limiting their usefulness in a manufacturing or field environment.

THz spectroscopy systems, on the other hand, are based on absorption of a generated THz-frequency signal (vs. Raman scattering) and capable of probing the same "low frequency/THz" energy regimes, but are generally constrained to a small spectral range (0-4 THz), limiting their ability to see the complete "fingerprint region" or chemical composition of a substance. THz spectroscopy techniques may also require special sample preparation, temperature control, and/or may be susceptible to moisture and water content, as well as being relatively expensive compared to the other techniques.

Finally, XRD systems may be extremely useful for determining the atomic and molecular structure of a crystal or biological molecule, but typically require significant sample preparation and are destructive in nature, therefore limiting their use in many manufacturing and process control applications.

SUMMARY

This summary is provided to introduce a selection of concepts in a simplified form that are further described in the Detailed Description below. This summary is not intended to identify key features or essential features of the claimed subject matter, nor is it intended to be used as an aid in determining the scope of the claimed subject matter.

The present disclosure is related to approaches for identification and analysis of materials and molecular structures. Specifically, an apparatus for identification and analysis of materials and molecular structures may comprise a laser. The laser may include an amplified spontaneous emission (ASE)-suppressed laser excitation source. The apparatus may further comprise a plurality of filters. The plurality of filters may include reflective volume holographic grating blocking filters. The apparatus may also comprise optical units and an optical spectrometer. The optical units may be configured to deliver excitation energy to a sample substance, and to capture Raman signal scattering from the sample substance. The optical spectrometer may be disposed in a path of the Raman signal and configured to measure a spectrum of the Raman signal and generate a detection signal. Finally, the apparatus may comprise a processing unit configured to analyze the spectrum.

According to another approach of the present disclosure, there is provided a method for identification and analysis of materials and molecular structures. The method may comprise providing a laser including an ASE-suppressed laser excitation source. Furthermore, a plurality of filters may be provided. The plurality of filters may include reflective volume holographic grating blocking filters. The method may further comprise providing optical units and an optical spectrometer. The optical units may be configured to deliver excitation energy to a sample substance, and to capture Raman signal scattering from the sample substance. The optical spectrometer may be disposed in a path of the Raman signal and configured to measure a spectrum of the Raman signal and generate a detection signal. Finally, the method may comprise providing a processing unit configured to analyze the spectrum.

BRIEF DESCRIPTION OF THE DRAWINGS

Embodiments are illustrated by way of example, and not by limitation, in the figures of the accompanying drawings, in which like references indicate similar elements and in which.

DETAILED DESCRIPTION

Figure 1:
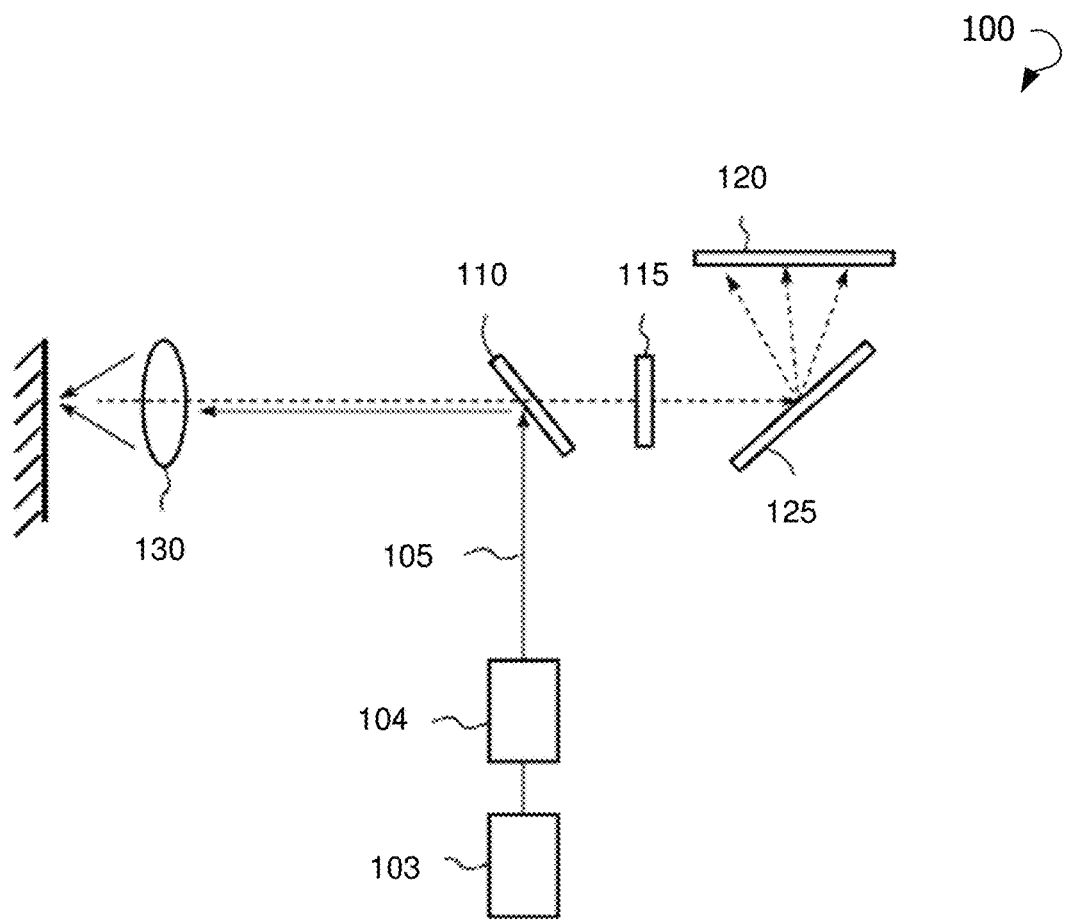
FIG. 1 shows a diagram of a prior art apparatus for identification and analysis of materials and molecular structures.

The following detailed description includes references to the accompanying drawings, which form a part of the detailed description. The drawings show illustrations in accordance with exemplary embodiments. These exemplary embodiments, which are also referred to herein as "examples," are described in enough detail to enable those skilled in the art to practice the present subject matter. The embodiments can be combined, other embodiments can be utilized, or structural, logical, and electrical changes can be made without departing from the scope of what is claimed. The following detailed description is therefore not to be taken in a limiting sense, and the scope is defined by the appended claims and their equivalents. In this document, the terms "a" and "an" are used, as is common in patent documents, to include one or more than one. In this document, the term "or" is used to refer to a nonexclusive "or," such that "A or B" includes "A but not B," "B but not A," and "A and B," unless otherwise indicated.

The present disclosure relates to efficient ways of implementing identification and analysis of materials and molecular structures and provides a system and a method for combined, simultaneous chemical and structural analysis of a substance using low-frequency Stokes and anti-Stokes Raman spectroscopy, greatly simplifying and reducing the cost of analysis, while improving sensitivity and reliability of the measurements. In particular, the system and method may reduce the cost, time, and complexity of polymorph screening and identification, especially for pharmaceutical ingredients and compounds, and for chemical and forensic analysis in general.

In particular, the present disclosure relates to capturing low-frequency Stokes and anti-Stokes signals in Raman analysis that may improve the sensitivity and reliability of the Raman spectroscopy measurement, by adding distinguishing and complementary spectral information to chemical detection and analysis algorithms. Furthermore, the spectral signatures in the low-frequency regime may be indicative of methods of manufacture or formulation that are valuable in forensic analysis, counterfeit detection, and explosives detection. Observation of low-frequency signals may also enable real-time identification of phase changes of materials. Furthermore, archeological and mineralogical analyses may also be advantageous due to the strong low-frequency signals associated with the mostly crystalline materials.

Anti-Stokes shifts are unique to Raman spectrometers: THz spectrometers do not stimulate such symmetrical spectral shifts. Anti-Stokes shifts are symmetrical to the Stokes shifts (albeit with reduced intensities according to the Boltzmann distribution), and remain fairly strong in the low-frequency regime, i.e. below 200 $cm^{-1}$. (Note that all mentions of spectral shift in this disclosure, whether in units of $cm^{-1}$ or THz, are measured relative to an excitation, or Rayleigh, wavelength). Due to their symmetry, these signals may be "added" to the low-frequency Stokes shifts, helping to confirm and strengthen the SNR of the measurement. Comparison of Stokes to anti-Stokes shifts may also be used as an indicator of the temperature of the substance under examination, useful for probing liquids and gasses. Unfortunately, simultaneous capture of low-frequency signals has heretofore been impossible with most Raman systems. In particular, multi-stage/cascaded Raman systems, which may be configured to acquire anti-Stokes signals, may be capable of measuring only one shift type (Stokes or anti-Stokes) at a time. Furthermore, typical notch-filter based Raman systems may lack the ultra-narrow filter bandwidths required to capture low-frequency signals.

Ultra-narrow-band volume holographic grating (VHG) filter technology may enable Raman spectrometer systems that are capable of rapid, simultaneous acquisition of both low frequency, Stokes and anti-Stokes Raman spectra in the 5-200 $cm^{-1}$ region, without compromising higher-frequency spectral signals to beyond 3,000 $cm^{-1}$. These systems may be based on a wavelength-stabilized laser source, a multiplicity of VHG filters, and a single stage spectrograph.

Several other factors may affect the ability of the system to adequately attenuate the Rayleigh signal and capture adequate Raman signal for analysis, and to ensure reliable and reproducible performance. These factors may include, but are not limited to, optical alignment, reduction of ASE noise, calibration, matching and synchronization of the laser and filter wavelengths, spatial filtering, and sample positioning. The system may also be built in a fiber-coupled probe configuration, for easy incorporation into vessels or for handheld use.

Prior art apparatus may enable efficient capture and filtering of Raman spectra in both the Stokes low-frequency Raman and fingerprint regimes (5 $cm^{-1}$ to 5000 $cm^{-1}$, or 150 GHz to 150 THz), and anti-Stokes Raman low-frequency and fingerprint regimes (−5 $cm^{-1}$ to −5000 $cm^{-1}$). FIG. 1 shows a schematic representation of an apparatus 100 for Raman spectroscopy described in the prior art. A laser source 103 may be collimated and ASE filtered by an assembly 104. The ASE filtered beam 105 may be reflected by a dichroic beam-splitter 110 towards a lens assembly or optical unit 130 that may focus the laser beam onto a sample under examination. The dichroic beam-splitter 110 may reflect the laser beam and may be transparent to other wavelengths. The signal beam generated from the sample as a result of the excitation laser beam (fluorescence, Raman) as well as the backscattering of the laser may be recollimated by the same lens/optical unit assembly 130. The signal may be transmitted through the dichroic beam-splitter 110 and incident on the volume holographic blocking notch filter assembly (VHBF) 115. Further spatial beam filters may be incorporated in the path of the signal beam to create a confocal system. After passing the VHBF assembly, the laser light may be rejected and the Raman, fluorescence or any other signal generated by the excitation laser may impinge on a dispersive element 125 such as, for example, a diffraction grating. The spectrally dispersed signal may be then received by an array of photodetectors 120.

However, in order to achieve optimal system-level performance, attention must be paid to laser and spectrometer specifications and overall optical layout. Because of the ultra-narrowband filter performance, laser excitation sources must have extremely narrow, stable line widths, and be free of ASE noise that can be comparable to (or even orders of magnitude larger than) the Raman signals of interest.

In the case of diode or diode-pumped lasers, closely matched ultra-narrowband ASE filters (also made from VHGs) may be required. Additionally, to preserve system throughput, careful attention to optics may be critical. For example, using a 90/10 VHG-based narrowband beam-splitter may boost, up to fourfold, overall system output.

Finally, the single-stage spectrometer may be configured to have sufficient spectral resolution to observe the low-energy transitions of interest for the specific material under test, and the grating and detector may be aligned to allow for capture of both Stokes and anti-Stokes signals. For most applications, it may be beneficial to have a system resolution on the order of ~1-5 $cm^{-1}$ (30-150 GHz) in order to capture sufficient data over the entire low-frequency regime for analysis. A conventional single-stage spectrometer with greater than 300 mm focal length and a 1200-1800 lines/mm grating may typically provide spectral resolution on this order. However, any dispersive spectrometer may be used as well. It should be noted that simply increasing the pitch of the dispersive grating inside the spectrometer may not always improve spectral resolution, as it may lead to increased aberrations in the beam that may degrade the effective resolution.

Figure 2:
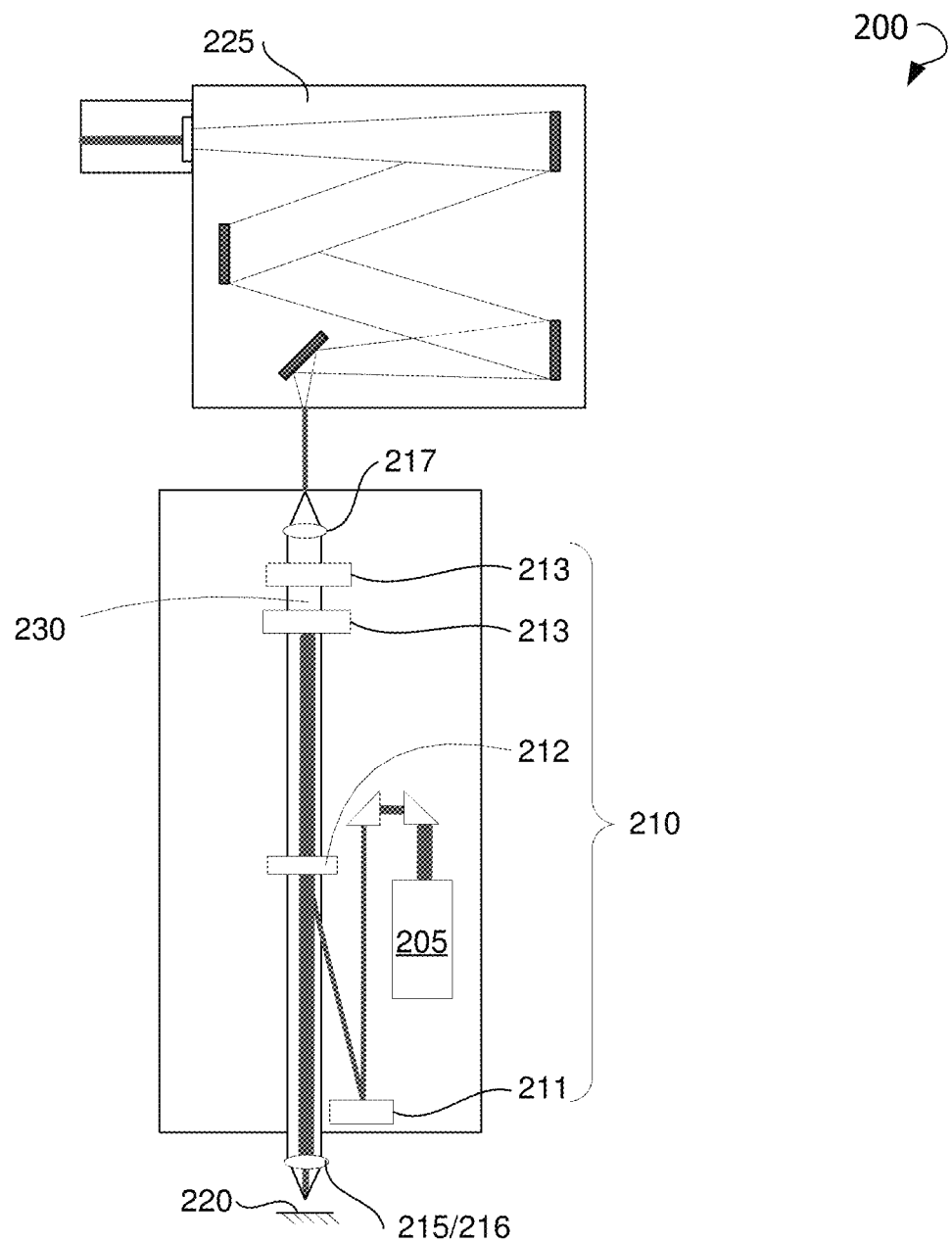
FIG. 2 is a diagram of an apparatus for identification and analysis of materials and molecular structures, according to an exemplary embodiment.

FIG. 2 illustrates an apparatus 200 for identification and analysis of materials and molecular structures. The apparatus 200 may comprise a laser 205. The laser 205 may include an ASE-suppressed laser excitation source. The laser 205 may be fiber-coupled or collimated. The laser may be spectrally narrowed to less than the bandwidth of the VHG blocking filters.

The apparatus 200 may further comprise a plurality of filters 210. The filters 210 may include reflective VHG blocking filters. In an exemplary embodiment, the filters 210 may include a VHG ASE filter 211, a VHG 90/10 beam-splitter filter 212, a VHG notch filter 213, etc. The filters 210 may have a cumulative optical density of at least 4.

The apparatus 200 may comprise one or more optical units 215 and 216. The optical unit 215 may be configured to deliver excitation energy to a sample substance 220, and optical unit 216 may capture Raman signal scattering from the sample substance 220. In an exemplary embodiment, the functions of optical units 215 and 216 may be accomplished with a single optical unit. In an exemplary embodiment, the sample substance 220 may be selected from a group comprising: a polymorphic, polyamorphous, allotropic, isomeric, isotopologous or conformational element, compound or substance; a pharmaceutical or biopharmaceutical compound, an explosive agent, a biological substance, a cellular substance, a chemically hazardous substance, a radiological substance, a mineralogical substance, a nuclear material, a radiological material, a semiconductor material, a photovoltaic material, an electronic material, and so forth.

The apparatus 200 may comprise an optical spectrometer 225. An optical unit 217 may be configured to optically couple the captured and filtered Raman signal, 230, which may be free space or fiber coupled, into the spectrometer 225, which may be configured to measure a spectrum of the Raman signal and generate a detection signal. The optical spectrometer 225 may be disposed in a path of the filtered Raman signal 230 filtered by the filters 210. The optical spectrometer 225 may be configured to collect low-frequency Stokes and anti-Stokes Raman spectra, including spectral shifts of $\pm 5$ $cm^{-1}$ to $\pm 200$ $cm^{-1}$ relative to the Rayleigh (or excitation) wavelength. In an exemplary embodiment, the optical spectrometer 225 may be configured to additionally collect Raman spectral shifts in the fingerprint regions from $\pm 200$ $cm^{-1}$ to $\pm 5000$ $cm^{-1}$.

The apparatus 200 may comprise a processing unit (not shown) configured to analyze the spectrum. In an exemplary embodiment, the analysis of the spectrum may include discriminating between various polymorphic forms, amorphous and crystalline phases of materials of the sample substance and detecting, identifying, characterizing, and monitoring a variety of structural characteristics of the sample substance, for example: crystalline orientation of the sample substance, strain or defects in the sample substance, and so forth. In further exemplary embodiments, the analysis of the spectrum may include one or more of the following: referencing in a look-up table associated with chemical or structural material property identification, go/no-go testing, pass/fail testing, and so forth.

FIG. 2 illustrates an exemplary embodiment in which the laser 205 and the plurality of filters 210 may be configured as a single unit optically coupled, via free-space or fiber coupling, to the optical spectrometer 225.

Figure 3:
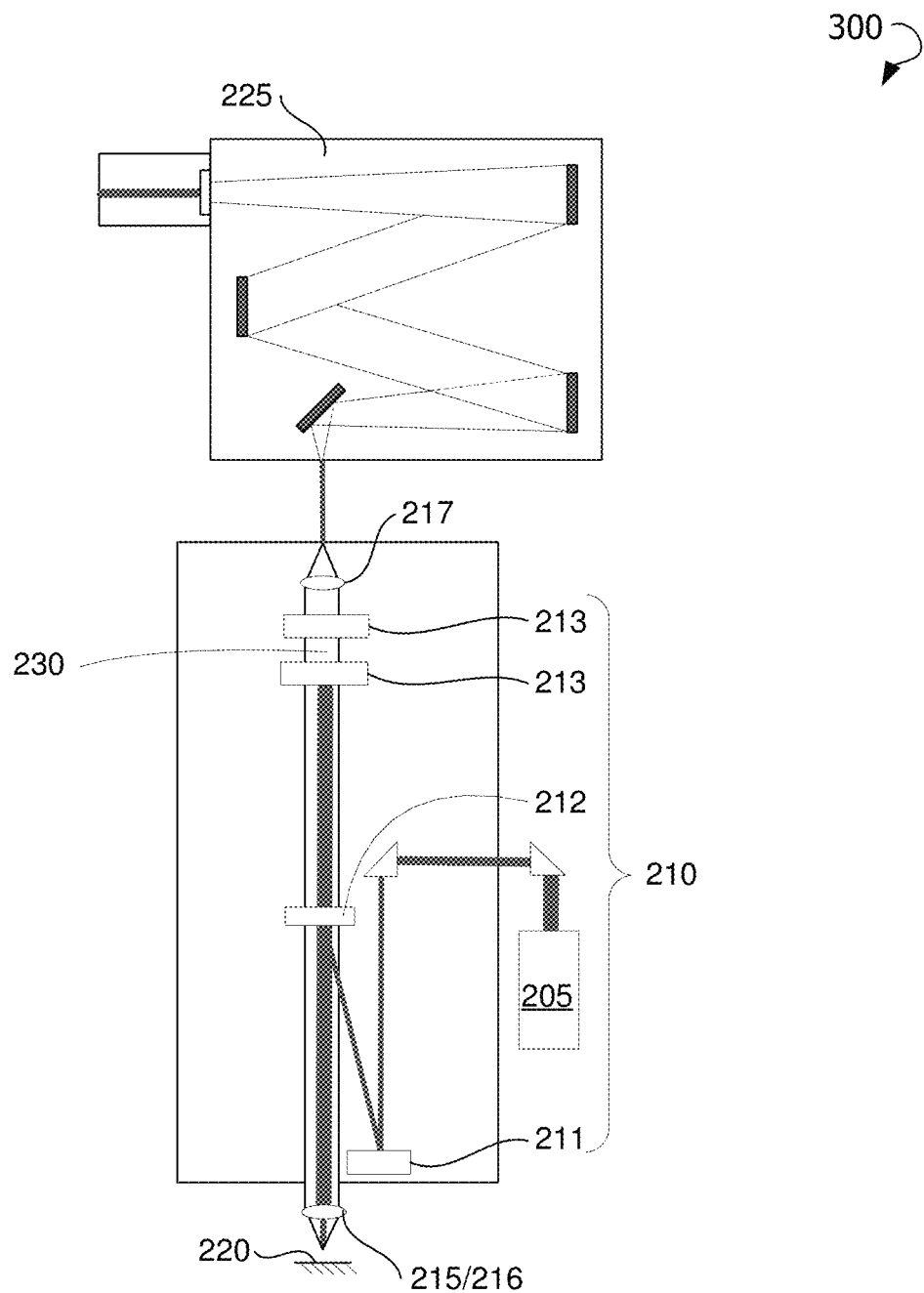
FIG. 3 is a diagram of an apparatus for identification and analysis of materials and molecular structures, according to an exemplary embodiment.
Figure 4:
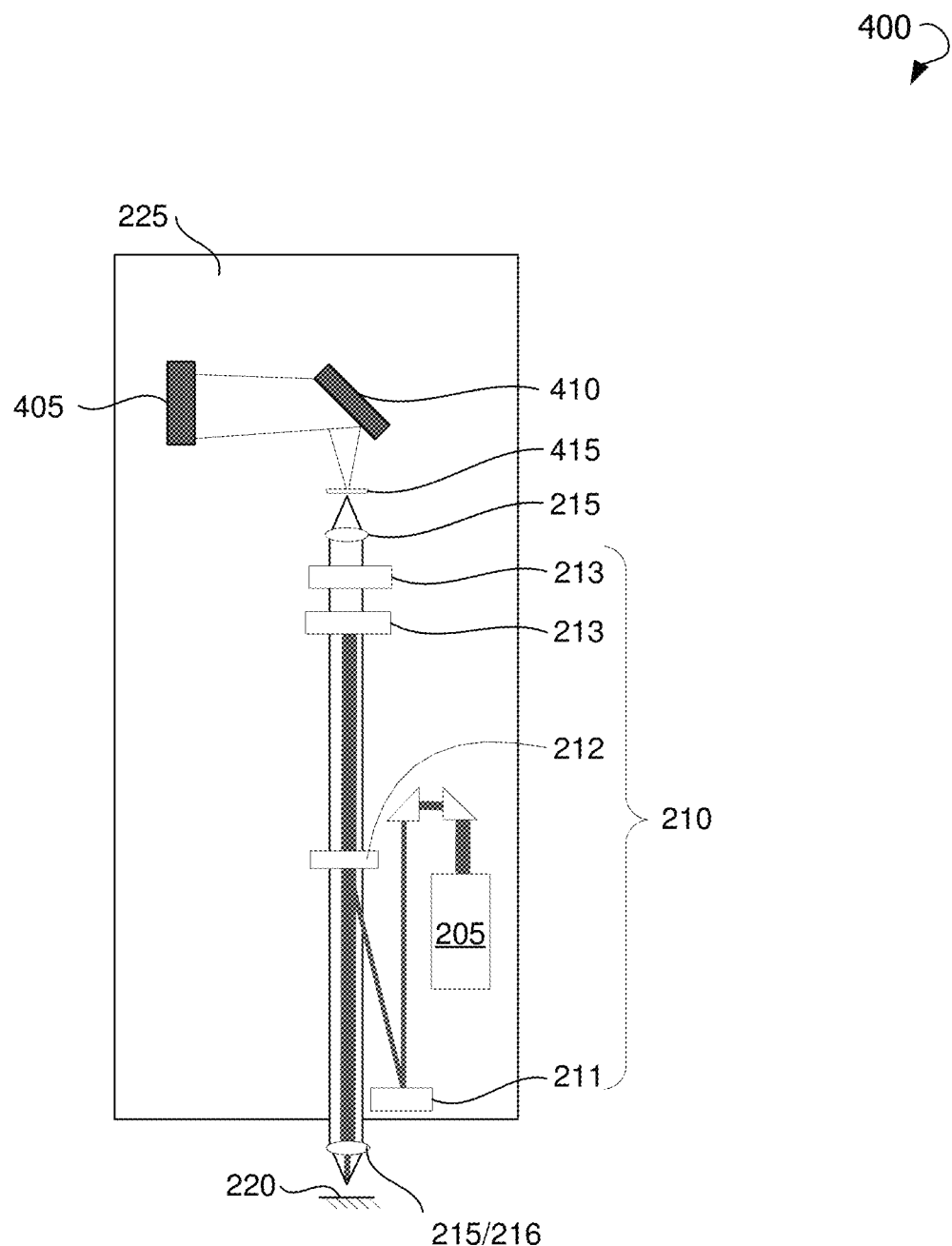
FIG. 4 is a diagram of an apparatus for identification and analysis of materials and molecular structures, according to an exemplary embodiment.

In a further exemplary embodiment of an apparatus 300 illustrated in FIG. 3, the laser 205, the plurality of filters 210, and the optical spectrometer 225 may be configured as individual units optically coupled via free-space or fiber coupling to each other. FIG. 4 illustrates a further exemplary embodiment, in which the laser 205, the plurality of filters 210, and the optical spectrometer 225 are configured as a single unit. The apparatus 400 may comprise a charge coupled device (CCD) detector 405, a dispersing grating 410, and a spatial filter 415. In the embodiments shown in FIG. 2 and FIG. 3, the plurality of filters 210 or the single unit comprising the integrated laser 205 and the plurality of filters 210 unit may be miniaturized into a probe for more convenient field use and to facilitate portability or attachment to formulation or processing equipment. The embodiment shown in FIG. 4, which includes all elements configured as a single unit, may also be miniaturized into a probe for more convenient field use and to facilitate portability or attachment to formulation or processing equipment.

Figure 5A:
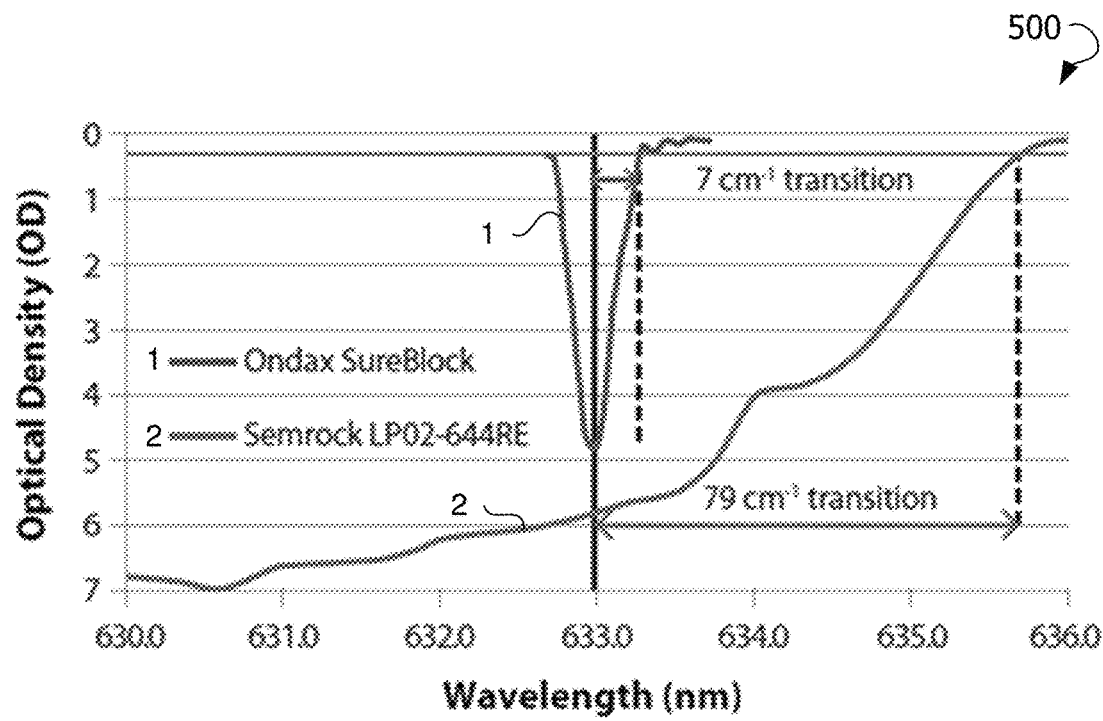
FIG. 5A is a diagram illustrating transition widths of a volume holographic filter and a sample filter.
Figure 5B:
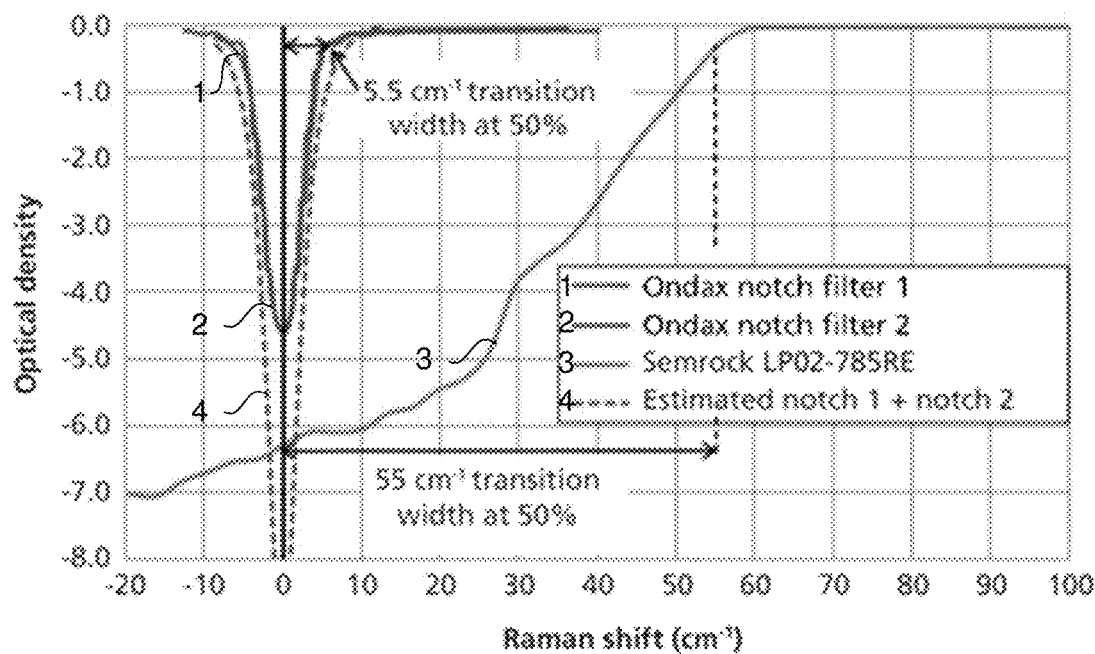
FIG. 5B is a diagram illustrating transition widths of a volume holographic filter and sample filters.
Figure 6:
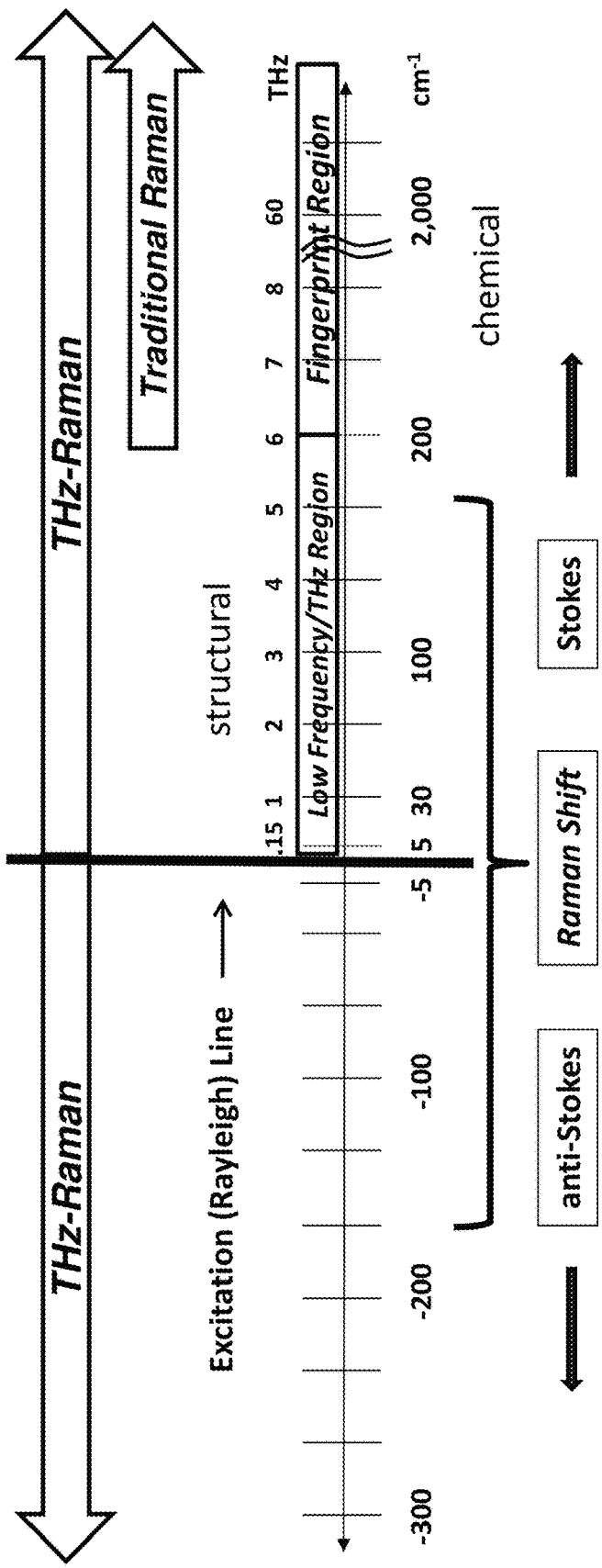
FIG. 6 is a diagram illustrating fingerprint, low-frequency, and anti-Stokes Raman regimes.

Each VHG filter may have a notch profile that may be designed to diffract only one specific wavelength matching the laser while transmitting all other wavelengths. These VHGs may be extremely robust "solid-state" gratings produced in a photosensitive glass, giving them all the transmission properties of optical glass, yet extremely high diffraction efficiency (or reflectivity) over a very narrow wavelength range, and may deliver unlimited lifetime compared to VHGs manufactured from non-glass materials such as polymers and gels. The ultra-narrow transition bandwidth of each of these notch filters may enable extremely high attenuation of the laser wavelength (more than OD 8 for the system), while maintaining very high transmission of nearby Raman signals beyond ~5 $cm^{-1}$ (as shown in diagram 500 of FIG. 5A and FIG. 5B). This combination of strong Rayleigh attenuation, high broadband transmission, and ultra-narrow bandwidth may enable the apparatus 200 to simultaneously capture both the intense low-frequency Raman bands and fingerprint region transitions, thereby improving the sensitivity and reliability of Raman for polymorph identification and other applications. FIG. 6 identifies the various accessible spectral ranges of Raman spectroscopy regions including fingerprint, low-frequency, and anti-Stokes regimes.

Figure 7A:
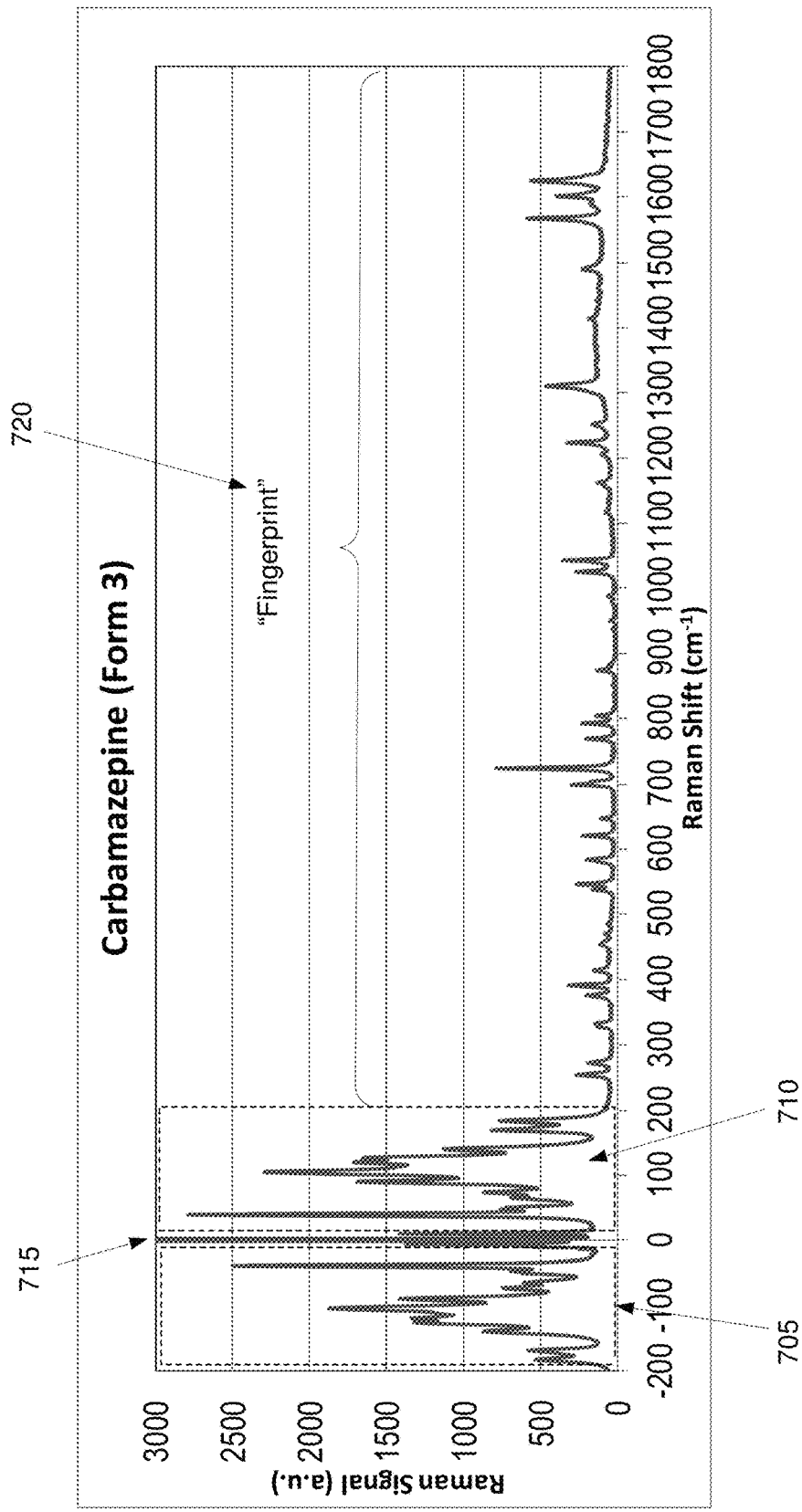
FIG. 7A is a diagram illustrating fingerprint, low-frequency, and anti-Stokes Raman regimes for Carbamazepine.

FIG. 7A illustrates Raman spectra showing fingerprint, low-frequency, and anti-Stokes Raman regimes for Carbamazepine Form 3 (CBZ). CBZ is an anticonvulsant and mood-stabilizing drug that is commonly prescribed in the treatment of epilepsy and bipolar disorder. FIG. 7A shows a low-frequency anti-Stokes zone 705 and a low-frequency Stokes zone 710 separated by a Rayleigh line 715. A fingerprint zone 720 is also shown.

Figure 7B:
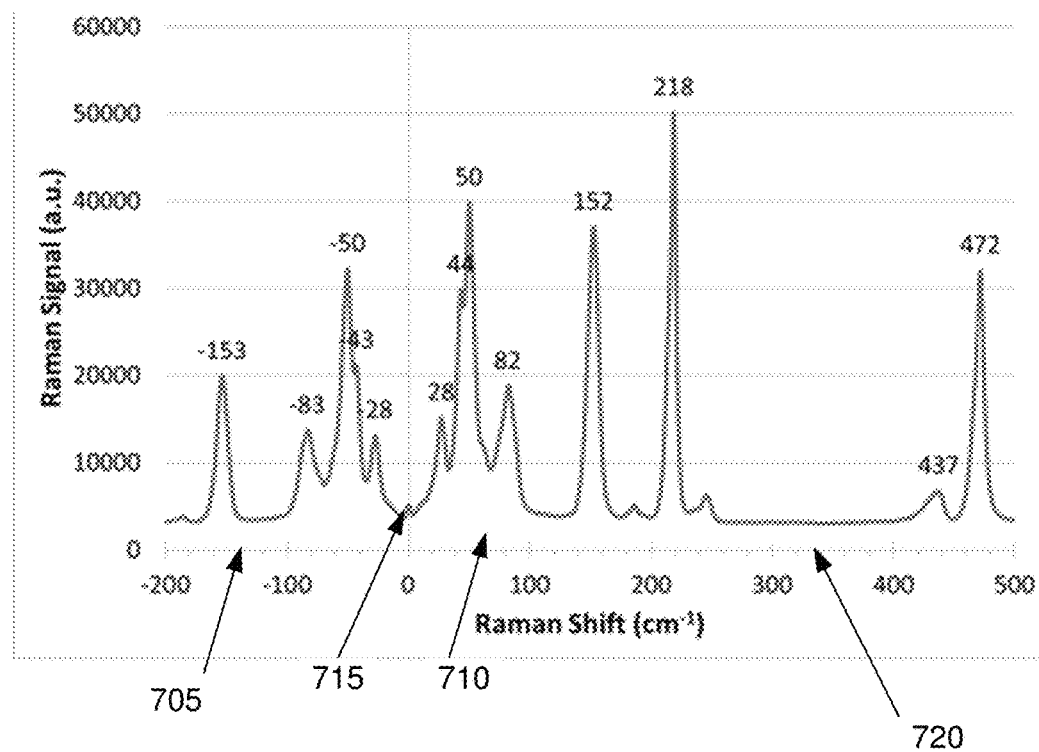
FIG. 7B a diagram illustrating fingerprint, low-frequency, and anti-Stokes Raman regimes for Sulfur.

FIG. 7B illustrates Raman spectra showing Stokes and anti-Stokes Raman regimes for Sulfur. FIG. 7B shows both symmetry and attenuation of anti-Stokes according to Boltzmann distribution. FIG. 7B also shows a low-frequency anti-Stokes zone 705 and a low-frequency Stokes zone 710 separated by a Rayleigh line 715. A fingerprint zone 720 is also shown.

Figure 8A:
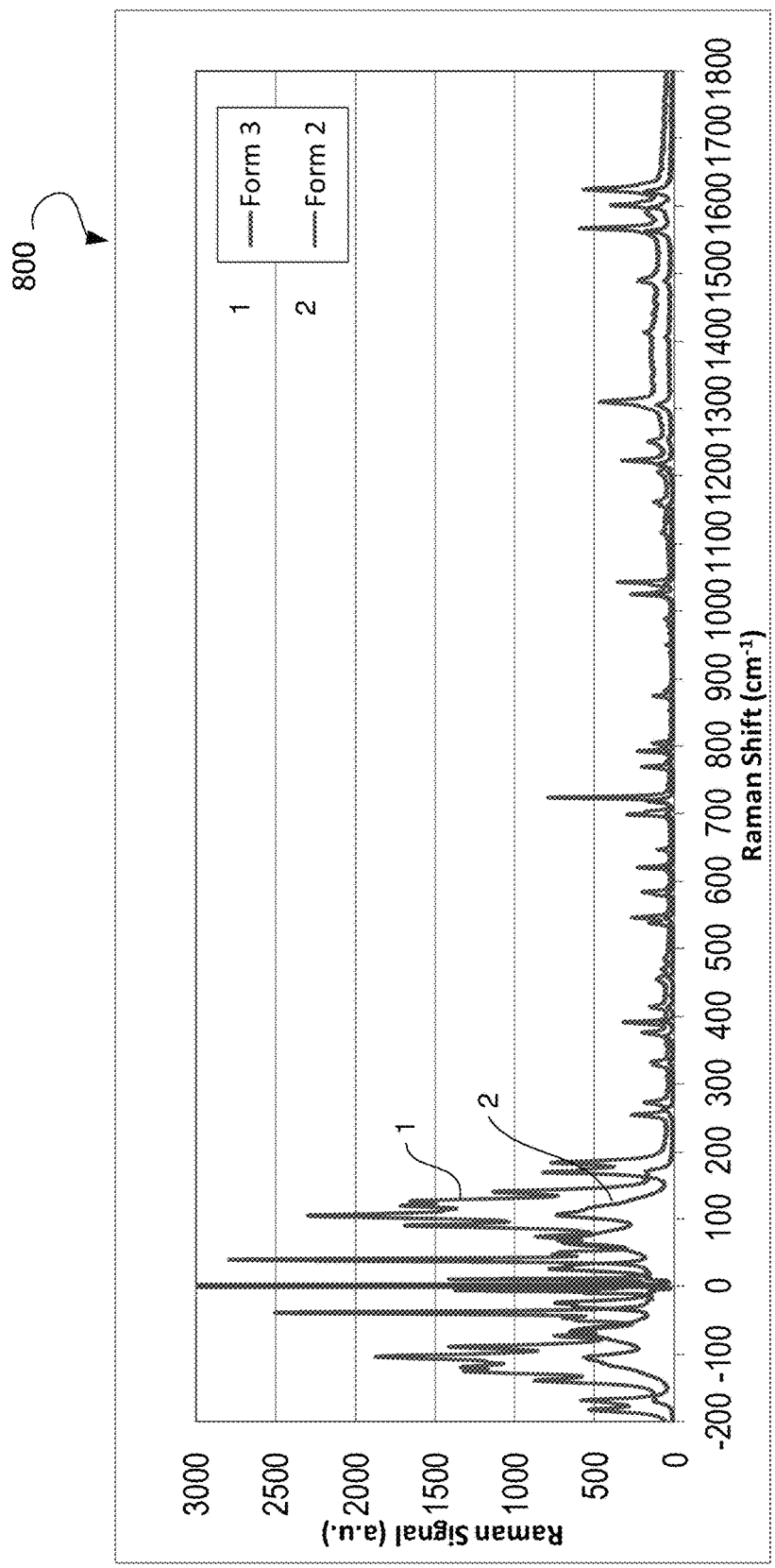
FIGS. 8A and 8B are diagrams illustrating low-frequency and anti-Stokes spectra for various polymorphs of Carbamazepine.
Figure 8B:
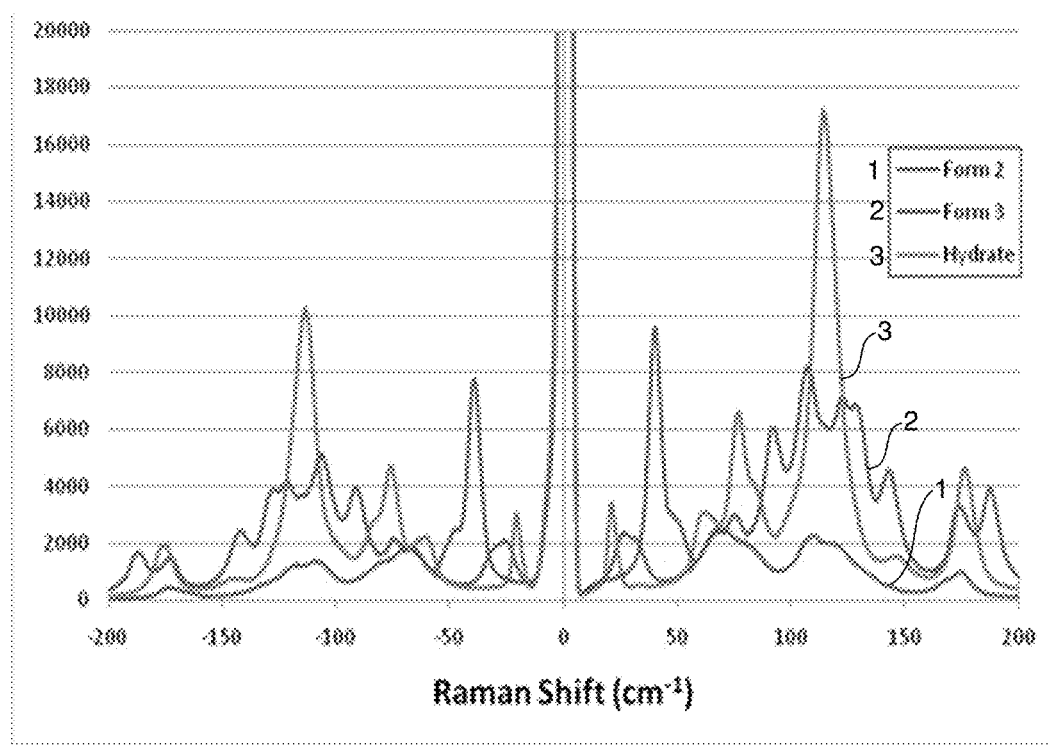

The resulting low-frequency/THz-Raman spectra captured by the apparatus 200 clearly show differentiating signals of polymorphic materials. FIG. 8A shows both low-frequency and "fingerprint" Raman signals for CBZ. CBZ has four different polymorphic forms as well as hydrates, with form 3 being the active pharmaceutical ingredient (API). FIG. 8A shows in diagram 800 spectra for Form 2 and Form 3, measured with the same excitation laser and integration conditions. Typical of many APIs that exhibit polymorphism, only one form (for CBZ, Form 3) is approved by the FDA, making it critical to monitor and control the API during formulation, processing, packaging and storage. Since the molecules have the same chemical composition, the fingerprint region signals 720 are quite similar, whereas the different structural forms of the polymorphs in regions 705 and 710 clearly present themselves as differences in the low frequency signals. FIG. 8B shows a close up of the low-frequency Stokes and anti-Stokes Raman spectra for Form 2 and Form 3, as well as the hydrated form, further highlighting these differences.

Figure 9A:
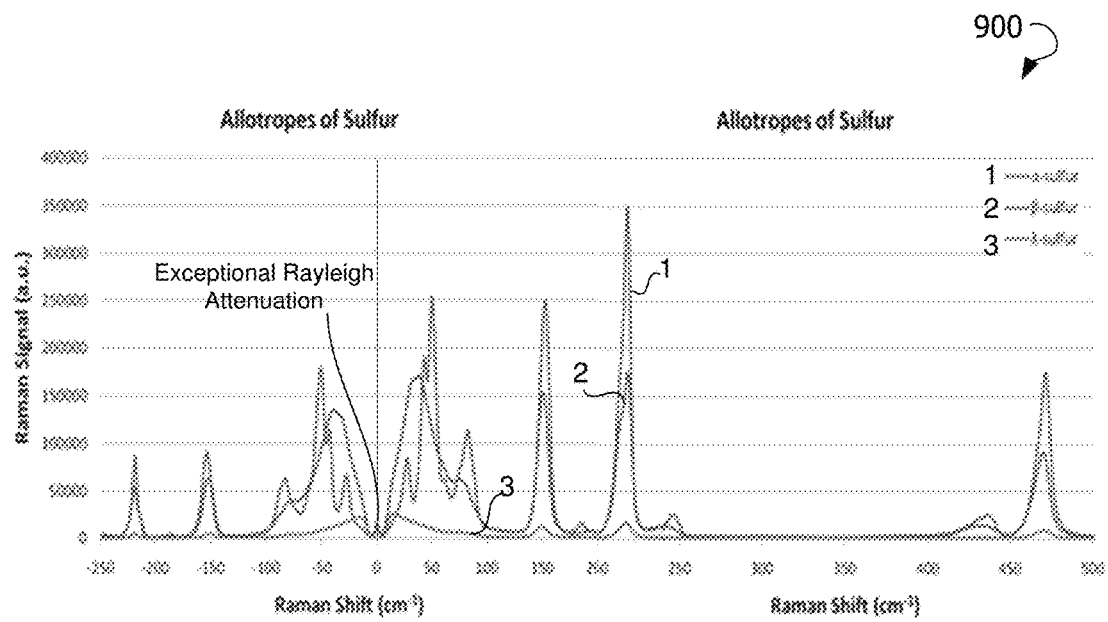
FIG. 9A is a diagram illustrating a low frequency Stokes and anti-Stokes spectrum for allotropes of Sulfur.

Two other examples of polymorph identification are Sulfur and 1,1,4,4-Tetraphenyl-1,3-butadiene (TPB). Sulfur forms over 30 different allotropes (polymorphs of a single chemical element), but the most common and easiest to produce are forms α, β, and λ. A sample of a-sulfur can be placed on a microscope slide and heated with a hot plate while measuring the Raman spectra with the described system as a function of temperature. The hot plate temperature can be monitored with a thermocouple. When the sample temperature is increased above 95.2° C., the form can change from α to β. Further increase of the temperature above the melting point at 115.21° C. can result in a second form change to λ. The corresponding Raman spectra for each form is plotted in diagram 900 of FIG. 9A. It should be noted that while there is a corresponding change in magnitude of the peaks in the Raman fingerprint region, there is no obvious shift in the position of the peaks. By comparison, the low-frequency region, particularly in the range of $\pm 100$ $cm^{-1}$ changes dramatically from one form to another in both magnitude and location of the peaks, enabling clear differentiation of the allotropes.

Figure 9B:
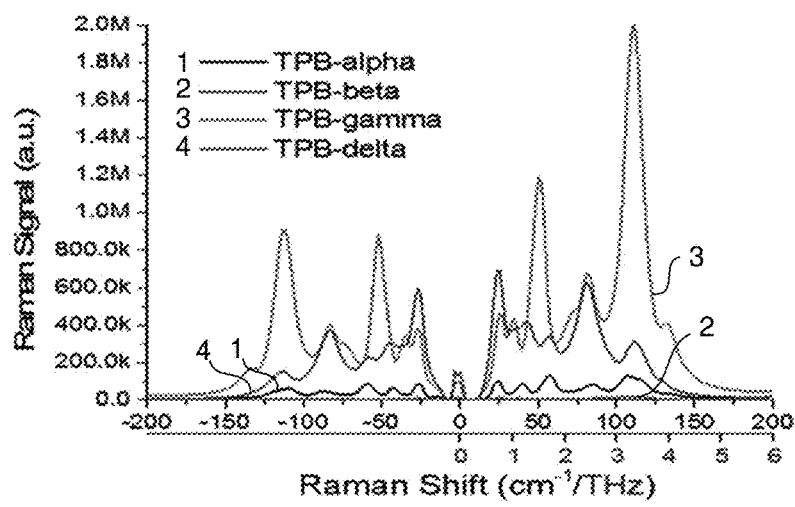
FIG. 9B is a diagram illustrating a low frequency Stokes and anti-Stokes Raman spectrum for various polymorphs of 1,1,4,4,-Tetraphenyl-1,3-butadiene (TPB).

TPB is a well-known blue-emitting organic electroluminescent molecule used in display applications, and is representative of a class of organic light-emitting materials being investigated for potential applications in micro- and opto-electronics. Characterization of these materials necessitates identification and analysis of molecular structure, crystal packing and lattice phonon dynamics, as well as charge transport and optical properties. Recent research using low-frequency Raman on this material shows that Raman spectroscopy is as an effective technique for identifying polymorphs and understanding their solid state properties. FIG. 9B shows the low-frequency Stokes and anti-Stokes spectra of several polymorphs of TPB.

Figure 10:
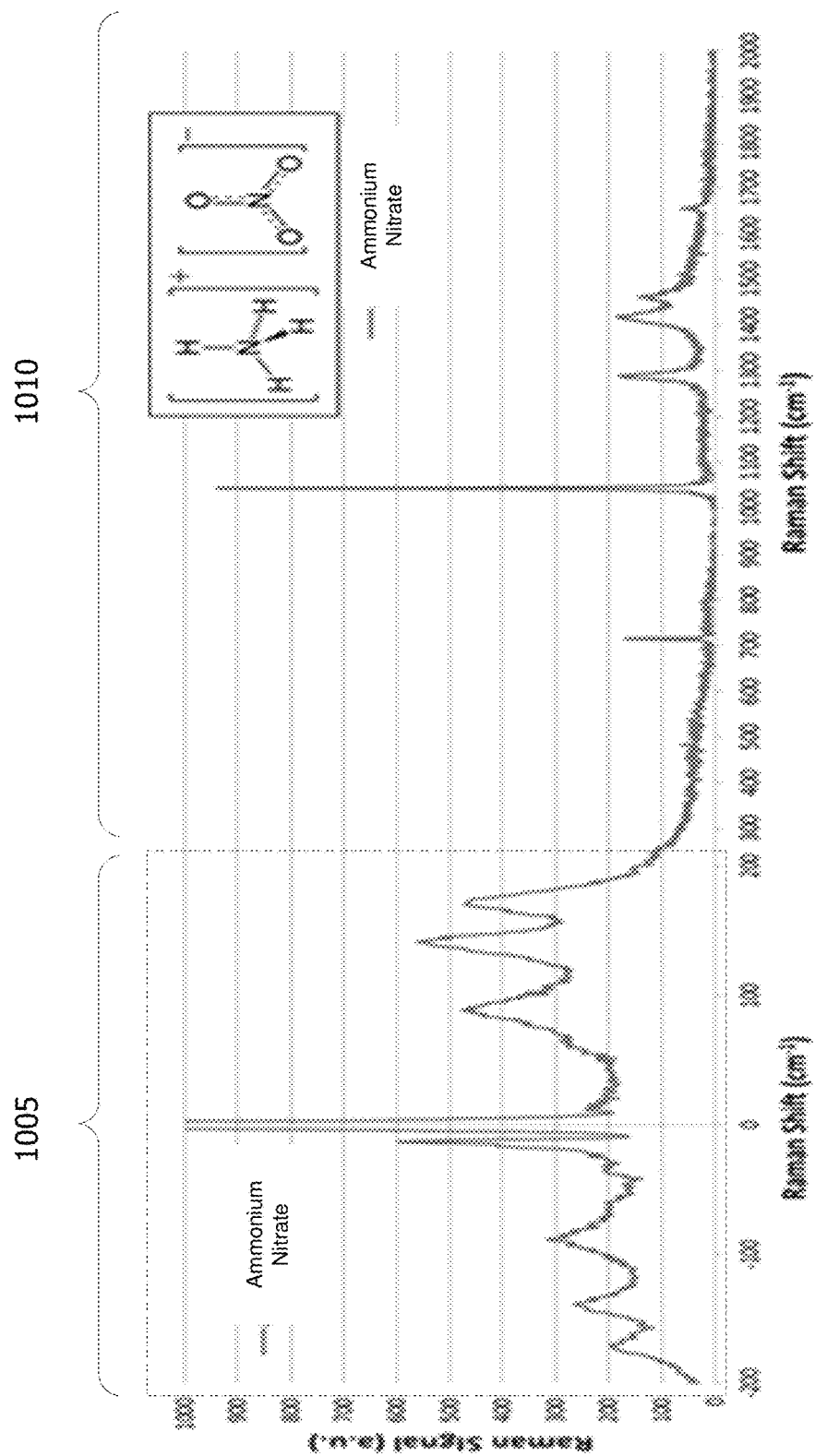
FIG. 10 is a diagram illustrating a fingerprint, low-frequency, and anti-Stokes Raman spectrum for Ammonium Nitrate.

Explosive or "energetic" materials, as well as many other hazardous chemicals and biological agents also tend to exhibit very strong low-frequency signatures. While Raman spectroscopy has been commercially accepted as a technique for explosives detection and analysis, there remain issues with reliability and reproducibility of results, e.g. false positives. The incorporation of low-frequency Raman spectra into the measurements can significantly enhance the sensitivity and confidence of detection. Many homemade explosive (HME) materials have also shown to exhibit very strong low-frequency signatures, with some exhibiting multiple isomers and polymorphs. FIG. 10 illustrates a THz-Raman (low frequency Stokes and anti-Stokes) region 1005, ±5 $cm^{-1}$ to 200 $cm^{-1}$, and a fingerprint region 1010, 200 $cm^{-1}$ to more than 2000 $cm^{-1}$ for Ammonium Nitrate. Broad peaks and anti-Stokes in THz-Raman region 1005 may mean increased number of photons for improved sensitivity. As shown, strong signals with excellent SNR can be detected in the low frequency regions. This additional information can be useful in detection, manufacture, and forensic analysis of energetic materials, CTAs and biological threats and materials.

The ability to analyze and attribute methods of manufacture or formulation of compounds, and by implication "sources of origin," is also of particular interest to both pharmaceutical manufacturers (for process control or counterfeit detection/surety testing), and government and police entities (for source attribution of HMEs and other explosive/Chemical Threat Agent (CTA) materials, or criminal evidence). Telltale signs or "signatures" of chemicals used during manufacture, processing methods and equipment, environment (temperature, humidity, pressure), as well as other active and inactive ingredients used in the manufacturing, handling or transport of substances may be detected or verified by the observation of low-frequency spectra.

Simultaneous capture and analysis of both Stokes and anti-Stokes spectra may also enhance the fidelity and reproducibility of Raman measurements including mitigating the effects of fluorescence (fluorescence is stronger on the Stokes side), boosting the overall signal by adding the Stokes and complementary anti-Stokes components together), and improving background subtraction algorithms (for example, atmospheric components may often show low-frequency signals and may be easily subtracted).

Raman spectroscopy is also being utilized for screening and analysis of biological tissues, for example for cancer detection. Low-frequency and anti-Stokes signals may also improve the detection, reproducibility, or capabilities of using Raman for these applications.

Isotopologues, defined as molecules that differ only in the isotopic nature of their atoms, will share their electronic structure and consequently be almost indistinguishable in their physical and chemical properties. However, since the vibrational modes are determined by both the shape and mass of the constituent atoms, isotopologues may exhibit different sets of vibrational modes, therefore exhibiting differences in their Raman spectral signatures. Low-frequency Raman spectra may improve detection, identification, and characterization of isotopologues using Raman analysis.

Figure 11:
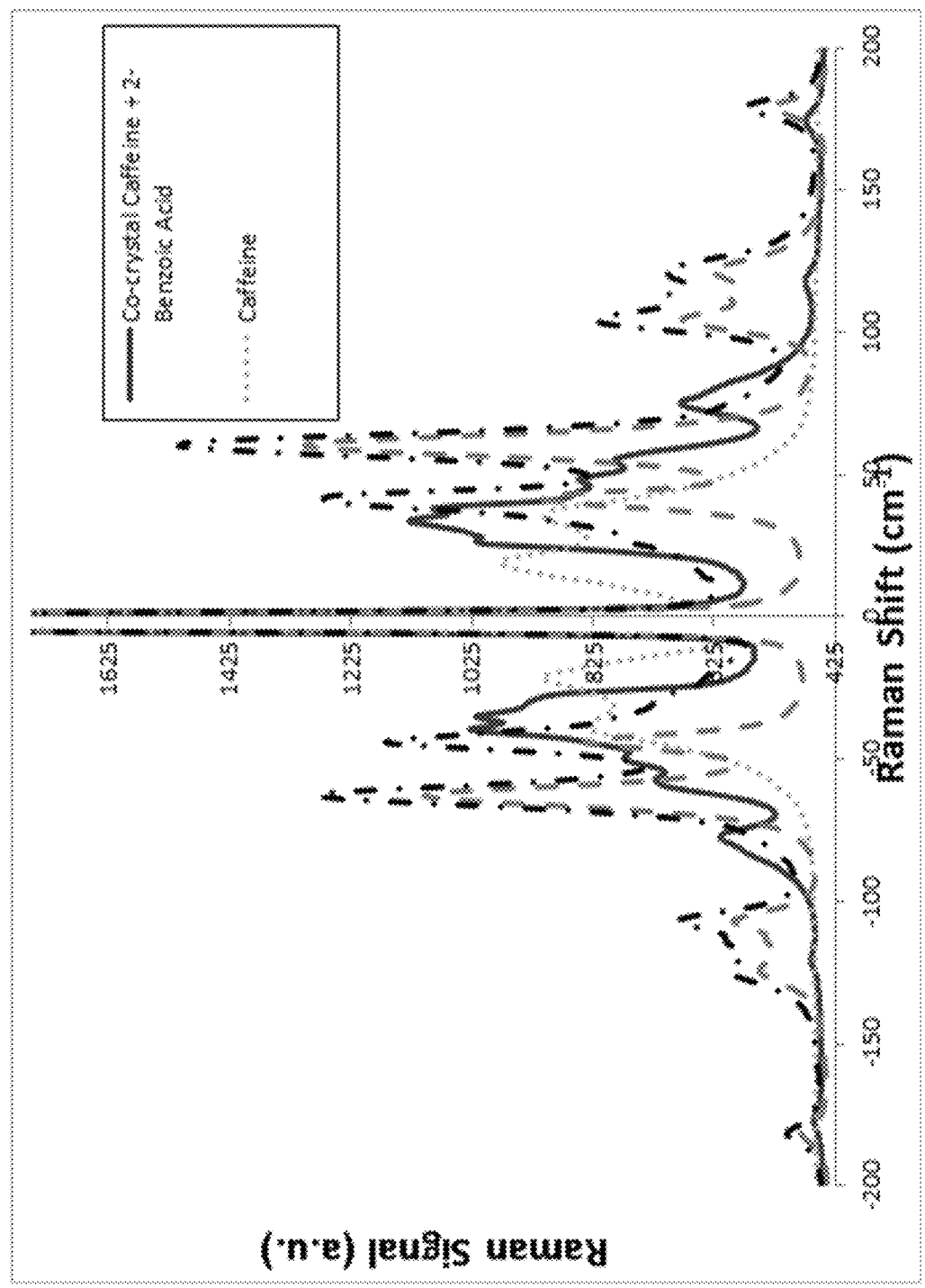
FIG. 11 is a diagram illustrating a fingerprint, low-frequency, and anti-Stokes Raman spectrum for Ammonium Nitrate.

Cocrystals are defined as substances consisting of two or more components, which form a unique crystalline structure having unique physical and chemical properties that differ from the properties of the individual components. The intermolecular interactions and resulting crystal structures also may exhibit uniquely identifying low-frequency Raman spectra. FIG. 11 shows clear differentiation between the low-frequency Stokes and anti-Stokes spectra of caffeine and Benzoic acid as individual substances, as well as blended and cocrystalline forms.

Figure 12:
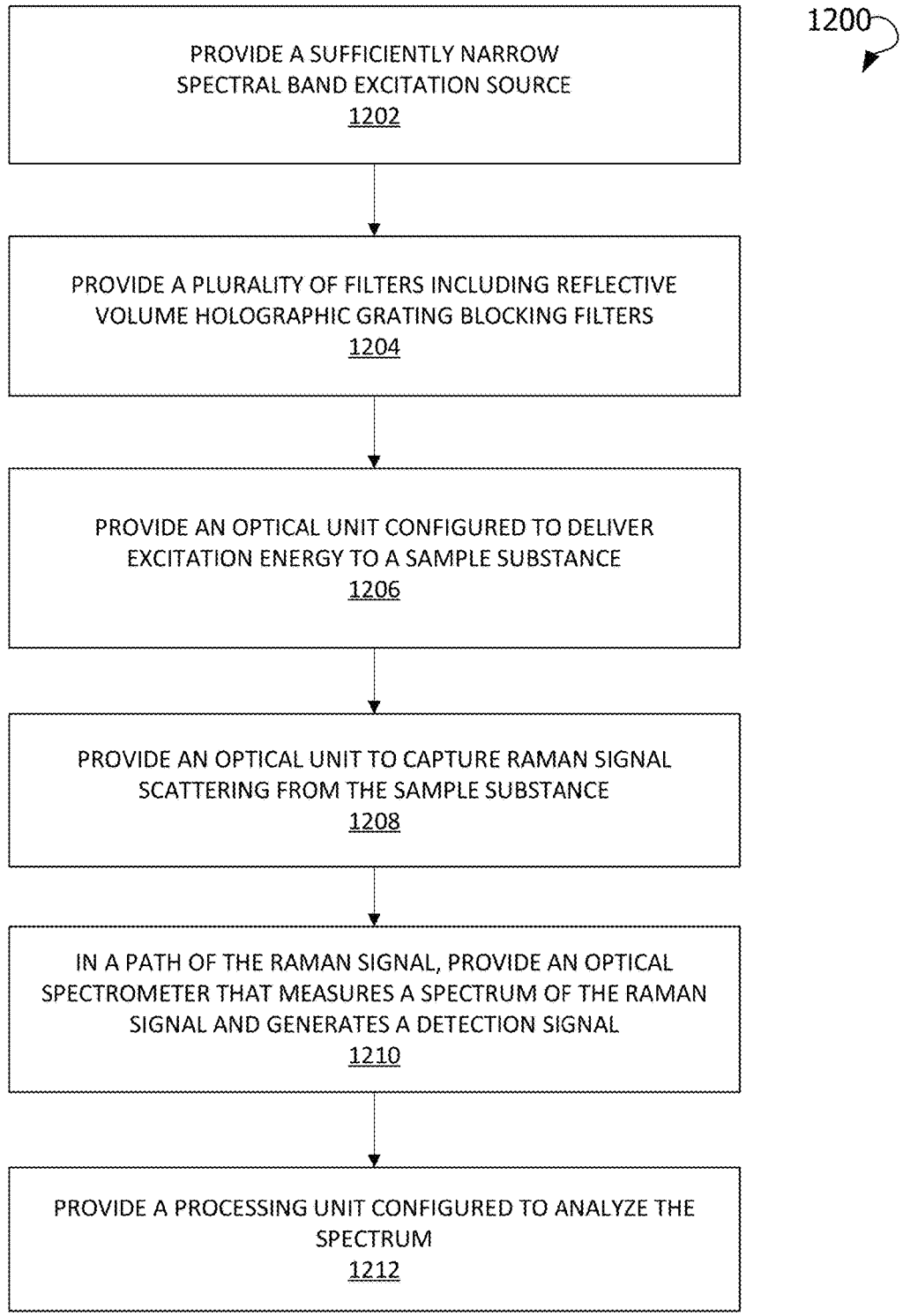
FIG. 12 is a diagram illustrating a method for identification and analysis of materials and molecular structures, according to an exemplary embodiment.

FIG. 12 is a flow chart illustrating a method 1200 for identification and analysis of materials and molecular structures. The method 1200 may commence at operation 1202 with providing an excitation source with sufficient spectral performance (e.g. bandwidth) to match the bandwidth of subsequent VHG blocking filters. The source may include an ASE-suppressed laser excitation source. In operation 1204, a plurality of filters may be provided. The plurality of filters may include reflective volume holographic grating blocking filters. Furthermore, the reflective volume holographic grating blocking filters may have a transition width of <50 $cm^{-1}$, and may have a cumulative optical density of at least 4.

The method 1200 may proceed to operation 1206, where an optical unit may be provided. The optical unit may be configured to deliver excitation energy to a sample substance. The method 1200 may proceed to operation 1208, where an optical unit may be provided. The optical unit may be configured to capture Raman signal scattering from the sample substance. The sample substance may include one or more of the following: a polymorphic, polyamorphous, allotropic, isotopologous, or conformational element, compound or substance; a pharmaceutical or biopharmaceutical compound, an explosive agent, a biological substance, a cellular substance, a chemically hazardous substance, a radiological substance, a mineralogical substance, a nuclear material, a radiological material, a semiconductor material, a photovoltaic material, an electronic material, and so forth.

In operation 1210, an optical spectrometer may be provided. The optical spectrometer may be disposed in a path of the Raman signal and configured to measure a spectrum of the Raman signal and generate a detection signal. The optical spectrometer may be configured to simultaneously collect low-frequency Stokes and anti-Stokes Raman spectra. The low-frequency Stokes and anti-Stokes Raman spectra may include ±5 $cm^{-1}$ to ±200 $cm^{-1}$ Raman spectrum. Furthermore, the optical spectrometer may be configured to collect ±200 $cm^{-1}$ to ±5000 $cm^{-1}$ Raman spectrum.

In an exemplary embodiment, the laser, the plurality of filters and the optical spectrometer may be configured as individual units optically coupled to each other. In further exemplary embodiments, the laser and the plurality of filters may be configured as a single unit and optically coupled to the optical spectrometer. In further exemplary embodiments, the plurality of filters and the optical spectrometer may be configured as a single unit, which may or may not include a laser source.

Furthermore, the method 1200 may comprise providing a processing unit configured to analyze the spectrum at operation 1212. The analysis of the spectrum may include one or more of the following: referencing in a look-up table associated with chemical or structural material property identification, go/no-go testing, pass/fail testing, discriminating between amorphous and crystalline phase of materials of the sample substance, and detecting, identifying, characterizing and monitoring of structural characteristics of the sample substance, which may include polymorphic forms, crystalline orientation, strain or defects in the sample substance, and so forth.

Thus, methods and systems for identification and analysis of materials and molecular structures have been described. Although the systems and methods have been described with reference to specific exemplary embodiments, it will be evident that various modifications and changes can be made to these exemplary embodiments without departing from the broader spirit and scope of the present application. Accordingly, the specification and drawings are to be regarded in an illustrative rather than a restrictive sense.

What is claimed is:

1. A method for identification and analysis of materials and molecular structures comprising:
providing a laser excitation source;
providing a plurality of filters, the plurality of filters including at least one reflective blocking filter with a transition width of <50 cm$^{-1}$;
providing at least one optical unit delivering excitation energy to a sample substance and capturing a Raman signal scattering from the sample substance, the captured Raman signal being at least in a spectral range of +20 cm$^{-1}$ to +200 cm$^{-1}$ or −20 cm$^{-1}$ to −200 cm$^{-1}$;
providing an optical spectrometer disposed in a path of the Raman signal, the optical spectrometer measuring a spectrum of the Raman signal and generating a detection signal, the optical spectrometer collecting low-frequency Stokes or anti-Stokes Raman spectra, the low-frequency Stokes or anti-Stokes Raman spectra being in a +20 cm$^{-1}$ to +200 cm$^{-1}$ or −20 cm$^{-1}$ to −200 cm$^{-1}$ Raman spectrum; and
providing a processing unit configured to analyze the captured Raman signal within the +20 cm$^{-1}$ to +200 cm$^{-1}$ or −20 cm$^{-1}$ to −200 cm$^{-1}$ portion of a spectrum of the sample substance, the analyzing of the +20 cm$^{-1}$ to +200 cm$^{-1}$ or −20 cm$^{-1}$ to −200 cm$^{-1}$ portion of the spectrum of the sample substance including measuring changes to at least one of peak shape and peak locations associated with structural characteristics or changes in form.

2. The method of claim 1 further comprising:
adding complementary components of the low-frequency Stokes or anti-Stokes Raman spectra to boost an overall signal, the optical spectrometer measuring a spectrum of the overall signal.

3. The method of claim 1, wherein the at least one reflective blocking filter has a cumulative optical density of at least 4.

4. The method of claim 1, wherein the laser excitation source is an ASE-suppressed laser.

5. The method of claim 1, wherein the optical spectrometer further collects Raman spectra in a fingerprint region.

6. The method of claim 1, wherein the sample substance includes at least one of a polymorphic, polyamorphous, allotropic, isomeric, isotopologous, cocrystalline, enantiomeric, polymeric, crystalline, and conformational element, compound, or substance.

7. The method of claim 1, wherein the sample substance includes at least one of a pharmaceutical or biopharmaceutical compound, an explosive agent, a biological substance, a cellular substance, a chemically hazardous substance, a radiological substance, a mineralogical substance, a nuclear material, a radiological material, a semiconductor material, a photovoltaic material, a polymer material, and an electronic material.

8. The method of claim 1, wherein the structural characteristics and/or changes in form include at least one of: phonon vibrational modes; polymorphic, allotropic, isomeric, conformational, isotopologic, or cocrystalline forms; amorphous and crystalline phases and phase changes; crystalline orientation; cocrystalline composition; rotational modes; physical properties; temperature; strain or defects; methods of manufacture; and environmental exposure.

9. The method of claim 1, wherein the laser excitation source, the plurality of filters, and the optical spectrometer are individual units optically coupled to each other.

10. The method of claim 1, wherein the laser excitation source and the plurality of filters are optically coupled to the optical spectrometer as a single unit.

11. The method of claim 1, wherein the laser excitation source, the plurality of filters, and the optical spectrometer are a single unit.

12. The method of claim 1, wherein the plurality of filters and the optical spectrometer are a single unit and the laser excitation source is optically coupled to the single unit.

13. The method of claim 1, wherein the optical spectrometer selects at least one of a peak and a signal in the spectrum of the Raman signal in the +20 cm$^{-1}$ to +200 cm$^{-1}$ or −20 cm$^{-1}$ to −200 cm$^{-1}$ portion, the at least one of the peak and the signal being associated with at least one material, compound, and molecular form, the processing unit determining at least one of a presence, an absence, and a concentration of the at least one material, compound, and molecular form using the at least one of the peak and the signal.

14. The method of claim 13, wherein the processing unit comprises a computer.

15. The method of claim 1, wherein the transition width is at least one of a separation from a 50% transmission point to a wavelength of the excitation energy and a separation from the 50% transmission point to a 0 cm$^{-1}$ reference point of the spectrum of the Raman signal.

* * * * *